(12) United States Patent
Bunick et al.

(10) Patent No.: US 7,371,405 B2
(45) Date of Patent: May 13, 2008

(54) CONSUMER CUSTOMIZED DOSAGE FORMS

(75) Inventors: Frank J. Bunick, Randolph, NJ (US); Stephan G. Wiet, Morristown, NJ (US); Stephen J. Saldutti, North Wales, PA (US); Paul D. Bisio, Lansdale, PA (US); Jeffrey Morrill, North Wales, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 704 days.

(21) Appl. No.: 10/743,127

(22) Filed: Dec. 22, 2003

(65) Prior Publication Data
US 2005/0136119 A1 Jun. 23, 2005

(51) Int. Cl.
*A61K 9/14* (2006.01)

(52) U.S. Cl. .................. 424/484; 424/439; 424/489

(58) Field of Classification Search .............. None
See application file for complete search history.

(56) References Cited

U.S. PATENT DOCUMENTS

| | | | |
|---|---|---|---|
| 4,071,614 A | | 1/1978 | Grimm, III |
| 4,520,014 A | | 5/1985 | Newsome et al. |
| 4,861,627 A | * | 8/1989 | Mathiowitz et al. ... 427/213.31 |
| 5,620,707 A | | 4/1997 | Sanker et al. |
| 6,428,808 B1 | * | 8/2002 | Buxton et al. ............. 424/451 |
| 6,482,433 B1 | | 11/2002 | DeRoss et al. |
| 6,806,256 B2 | * | 10/2004 | Ulrich et al. .............. 514/19 |
| 2003/0026872 A1 | * | 2/2003 | Dake et al. .................. 426/72 |
| 2005/0136105 A1 | | 6/2005 | Allen et al. |
| 2006/0165614 A1 | * | 7/2006 | Nelson et al. ............... 424/50 |

FOREIGN PATENT DOCUMENTS

| | | |
|---|---|---|
| EP | 0298740 A | 1/1989 |
| EP | 0570327 A | 11/1993 |
| GB | 2147501 A | 5/1985 |
| WO | WO 9713416 A1 * | 4/1997 |

OTHER PUBLICATIONS

Associated Press, www.cnn.com/2003/HEALTH/07/28 customized.drugs.ap/index.html.
Database WPI Section Ch, Week 200378 Derwent Publications Ltd., London, GB, AN 2002-845036 XP002327004 & WO 03/074086 A1 (Medrx Co Ltf) Sep. 12, 2003 abstract.
Chawla J et al: "Effect of Route of Administration on the Pharmacokinetic Behavior of Enantiomers of Nefopam and Desmethylnefopam" Therapeutic Drug Monitoring, New York, NY, US vol. 25, No. 2, Apr. 2003 pp. 203-210, XP008046826 ISSN: 0163-4356 p. 204, right hand column, lines 44, 45.
PCT Search Report PCT/US2004/042150 dated May 30, 2005.
PCT Search Report PCT/US2004/042398 dated Jun. 8, 2005.

* cited by examiner

*Primary Examiner*—S. Tran

(57) ABSTRACT

Customizable dosage forms are provided. The flavor, color, sweetness, or texture of the dosage forms may be customized directly by the consumer.

20 Claims, No Drawings

CONSUMER CUSTOMIZED DOSAGE FORMS

The invention provides a method of customizing dosage forms by the consumer.

BACKGROUND OF THE INVENTION

The taste, color and texture of pharmaceutical dosage forms are important factors in patient compliance with dosing regimens. Since pharmaceutically active ingredients often have unpleasant tastes or textures for example, a wealth of taste masking and texture masking technology has developed in the art. However, such technology is typically applied during manufacturing of dosage forms, and therefore not subject to a high degree of consumer customization. Unfortunately, different patients often prefer different product attributes, tire of certain product attributes. Pediatric patients can be especially finicky about taste and texture, making administration of medicine to them particularly difficult.

Pharmacists sometimes custom flavor dosage forms for patients. However, the current practice suffers from several limitations. First, not all flavoring agents are physically and/or chemically compatible with all of the excipients typically employed in liquid dosage forms, such as suspension vehicles. Accordingly, it is often necessary to test the compatibility and stability of known flavoring agents with the liquid dosage forms with which they are intended for combination. Second, the addition of commercially available flavor systems to a pre-flavored liquid product can result in flavor incompatibilities. Certain flavors can overwhelm others, or certain "off-notes" of one flavor can increase in the presence of another flavor. Third, the flavoring agents used by pharmacists are typically highly concentrated compositions that require professional training to use. They are unsuitable for use by a consumer.

A method for preparing a flavored liquid medicament, particularly a pediatric preparation, is disclosed in U.S. Pat. No. 6,428,808 B1. The method comprises addition of a flavoring vehicle to an unflavored liquid medicament that has an unacceptable taste.

Applicants have now discovered that pharmaceutical dosage forms may be customized directly by the consumer by providing customization agents that are physically and chemically compatible with the dosage forms, i.e., ready to use. These customization agents, specifically flavoring agents, sweetening agents, or texturizing agents, are suitable for combination with the dosage form just prior to administration. Flavoring agents in particular are advantageously compatible for adding to dosage forms already containing a first flavor, so that the dosage form is initially provided to the consumer with at least some flavor, which may be subsequently customized as desired prior to administration.

SUMMARY OF THE INVENTION

The invention provides a method of custom sweetening a pharmaceutical dosage form, comprising providing a consumer with a) a liquid pharmaceutical dosage form having a sweetness index of less than about 0.6, and b) a customization agent comprising a sweetening agent, said customization agent being physically and chemically compatible with said dosage form, such that the consumer may combine said customization agent with said dosage form to make a customized dosage form.

The invention also provides a method of custom flavoring a liquid pharmaceutical dosage form, comprising providing a consumer with a) a liquid pharmaceutical dosage form comprising a first flavoring agent, and b) a customization agent comprising a second flavoring agent, said customization agent being physically and chemically compatible with said dosage form, such that the consumer may combine said customization agent with said pharmaceutical dosage form to make a customized dosage form.

The invention further provides a kit comprising a) a first container containing one or more pharmaceutical dosage forms; and b) a second container containing one or more customization agents that are physically and chemically compatible with said dosage forms.

The invention also provides a liquid pharmaceutical dosage form comprising a liquid matrix containing an active ingredient, a first flavoring agent having a first flavor, and a plurality of particles comprising a second flavoring agent having a second flavor.

DETAILED DESCRIPTION OF THE INVENTION

As used herein, the term "dosage form" applies to any composition designed to contain a specific pre-determined amount (dose) of a certain ingredient, for example an active ingredient as defined below. The dosage form of the present invention is an orally administered liquid, solid, or semi-solid product for delivering a pharmaceutical active ingredient to the gastro-intestinal tract of a human. In one embodiment the dosage form is a liquid. It may be for example a syrup, suspension, solution, or emulsion. It may be provided in liquid form or provided to the consumer as a solid to be reconstituted into liquid form. In another embodiment, the dosage form of the present invention may be a multiparticulate solid such as a powder, sachet, or sprinkle. In another embodiment, the dosage form of the present invention may be a semisolid, such as a gel, pudding, or mousse. Preferably, the dosage form is an over-the-counter product, that is, sold without a physician's prescription.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetidine, nizatidine; proton pump inhibitors such as omeprazole or lansoprazole; gastrointestinal cytoprotectives, such as sucralfate and misoprostol; gastrointestinal prokinetics, such as prucalopride, antibiotics for Hpylori, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, one or more active ingredients may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, one or more active ingredients are selected from analgesics, anti-inflammatories, and antipyretics: e.g. non-steroidal anti-inflammatory drugs (NSAIDs), including propionic acid derivatives: e.g. ibuprofen, naproxen, ketoprofen and the like; acetic acid derivatives: e.g. indomethacin, diclofenac, sulindac, tolmetin, and the like; fenamic acid derivatives: e.g. mefanamic acid, meclofenamic acid, flufenamic acid, and the like; biphenylcarbodylic acid derivatives: e.g. diflunisal, flufenisal, and the like; and oxicams: e.g. piroxicam, sudoxicam, isoxicam, meloxicam, and the like. In a particularly preferred embodiment, the active ingredient is selected from propionic acid derivative NSAID: e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, at least one active ingredient may be selected from pseudoephedrine, phenylpropanolamine, chlorpheniramine, dextromethorphan, diphenhydramine, astemizole, terfenadine, fexofenadine, loratadine, desloratadine, doxilamine, norastemizole, cetirizine, mixtures thereof and pharmaceutically acceptable salts, esters, isomers, and mixtures thereof. In a particular embodiment, the active ingredient may be selected from fexofenadine, loratadine, desloratadine, terfenadine, astemizole, norastemizole, cetirizine, and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260. As used herein, the term "simethicone" refers to the broader class of polydimethylsiloxanes, including but not limited to simethicone and dimethicone. Examples of other water insoluble pharmaceutical active ingredients that can be used in accordance with the invention include but are not limited to the following examples: analgesics, such as APAP and ibuprofen; cardiovascular drugs, e.g. cardiac glycosides, clofibrate and probucol; hypoglycemic drugs; sedatives/hypnotics, e.g. barbiturates, disulfiram and glutethimide; antiepileptics, e.g., carbamazepine, mephenytoin, phenytoin and phensuximide; psychopharmacologic agents e.g. perphenazine; analgesic, antipyretic and anti-inflammatory agents, e.g. naproxen, oxycodone, indomethacin, and phenylbutazone; antineoplastic drugs such as lomustine; and antimicrobials such as erythromycin estolate.

The dosage form is provided to an end user consumer with a customization agent. The customization agent is physically and chemically compatible with the dosage form. As such, the customization agent may be readily combined with the dosage form by the consumer after purchase and prior to administration. Unlike known flavoring agents used by pharmacists, the present customization agent requires no special handling or measuring, and is formulated to be ready to use by the consumer.

Although the description herein refers to the combination of a single dosage form with a single customization agent, it should be understood that more than one dosage form or more than one customization agent may be used. Further, two or more coloring agents, or a flavoring agent and a texturizing agent, may be included in a single customization agent. Alternatively, a single customization agent may be added to a mix of two dosage forms, etc.

The dosage form and the customization agent are combined by the consumer. Such combination may be by addition of one to the other, optionally accompanied by mixing, stirring, shaking, or the like. Combination may be performed well before administration, on the order of hours or days, or just prior to administration. Preferably, combination is performed just prior e.g. within 30 minutes, more preferably immediately prior, e.g. within 5 minutes prior to administration. The dosage form and the customization agent may optionally be provided to the consumer with instructions for combination. Such instructions preferably direct the consumer to combine the dosage form and the customization agent just prior to administration. In one embodiment, instructions may include shaking or stirring. In another embodiment, mixing is not required. In one particular embodiment, the consumer is directed to sprinkle the customization agent on top of a measured dose of the dosage form. Advantageously, the combination of the dosage form and customization agent may be performed directly in the unit dose container from which the customized dosage form will be administered to the patient.

The customization agent may comprise for example one or more flavoring agents, flavor modifiers, sweetening agents, sensation agents, coloring agents, or texturizing agents. Suitable flavoring agents include those compounds and complex mixtures of compounds known in the art of flavor chemistry to impart desirable flavors to edible products. Suitable flavor modifiers include those compounds known in the art of flavor chemistry to modify the perception of taste of other compounds, for example bitterness masking agents, and the like. Suitable sweetening agents include sugars such as sucrose, glucose, fructose, and the like; polyhydric alcohols such as mannitol, xylitol, erythritol, sorbitol, maltitol and the like; and high intensity sweeteners such as saccharin, aspartame, acesulfame, sucralose, cyclamate, and pharmaceutically acceptable salts thereof; and mixtures thereof. Suitable sensation agents include those compounds and complex mixtures of compounds commercially available through flavor companies such as International Flavors and Fragrances, Inc., which are known to impart a cooling, warming, salivation-inducing, astringent, buzzing, or tingling effect to the tongue or oral or pharyngeal mucosa. Suitable coloring agents include FD&C dyes and lakes as known in the art.

The customization agent may be in solid, semi-solid, or liquid form. For example, the customization agent may be a solid such as particles, flaked films, crystals, powders (e.g. sachets), agglomerates, beads, strips, fibers, films, tablets, or capsules. The customization agent may be a liquid such as a syrup, suspension, solution, or emulsion. The customization agent may dissolve in the liquid dosage form or may be dispersed in the liquid dosage form.

In certain preferred embodiments, the customization agent is in the form of a flaked film. The flaked films may be used to deliver flavoring agents, flavor modifiers, sensation agents, texturizing agents, coloring agents, sweetening agents, and the like. In certain embodiments, the flaked films advantageously may be used to impart a long lasting second flavor due to their extended residence in the oral cavity after the liquid dosage form is swallowed. Additionally the flaked films do not impart a gritty texture to the liquid dosage form.

Suitable flaked films are commercially available from Watson Foods, as "edible glitters." These include "edible glitter" comprising gum arabic and FDA, EU, or Natural approved coloring agents or flavoring agents; "insoluble edible glitter" comprising sodium alginate and FDA, EU, or Natural approved coloring agents or flavoring agents; "slow soluble edible glitter WT-7474" comprising sodium alginate and FDA, EU, or Natural approved coloring agents or flavoring agents and optionally citric acid; and "soluble edible glitter F290" comprising gum arabic and FDA, EU, or Natural approved coloring agents or flavoring agents. Other suitable flaked films are commercially available from Aquafilm, LLC. The flaked films may be prepared by comminution of edible films comprising suitable film forming materials. Any film-former known in the pharmaceutical arts is suitable for preparing the flaked films of the present invention. Suitable film formers include but are not limited to gum arabic, pullulan, starch, maltodextrins, pectin, hydroxypropylmethylcellulose, alginates, carrageenans, and derivatives and combinations thereof. Suitable flaked films may range in length or width from about 4760 to about 590 microns (about 4 to about 30 mesh), e.g. about 2380 microns (about 8 mesh).

In certain optional embodiments in which the customization agent comprises flaked films, the flaked films may comprise multiple layers, e.g. they may be laminates comprising two or more film layers. Laminated layers are particularly useful as functional elements to control physical properties of the flaked films, for example bioadhesion, dissolution properties, etc. The laminated layers may further comprise holes or pores. In one particular embodiment, the customization agent is a single or multiple layer flaked film having a thickness from about 0.01 to about 0.25 mm, e.g. from about 0.02 to about 0.08 mm.

The flaked films are dispersed in the dosage form upon addition by the consumer, and preferably remain undissolved for some period of time until they are consumed by the patient. Preferably the flaked films remain substantially undissolved for at least about 1 minute, e.g. at least about 3 minutes, say at least about 5 minutes. By substantially undissolved, it is meant that the flaked films can be visually detected as particulate matter, and that they retain at least some of their flavor.

In one embodiment of the invention, the customization agent comprises a sweetening agent. Here, the initial dosage form may be provided with a sweetness index less than about 0.6. The addition of the customization agent comprising a sweetening agent increases the sweetness of the dosage form to at least about 0.9, e.g. at least about 1.0, say at least about 1.5, or at least about 2.0. As used herein, "sweetness index" is a term used to describe the level of sweetness of the dosage form relative to sucrose. Sucrose, defined as the standard, has a sweetness index of 1. For example, the sweetness indices of several known sweet compounds are listed below:

| | |
|---|---|
| Sorbitol | 0.54-0.7 |
| Dextrose | 0.6 |
| Mannitol | 0.7 |
| Sucrose | 1.0 |
| High Fructose Corn Syrup 55% | 1.0 |
| Xylitol | 1.0 |
| Fructose | 1.2-1.7 |
| Cyclamate | 30 |
| Aspartame | 180 |
| Acesulfame K | 200 |
| Saccharin | 300 |
| Sucralose | 600 |
| Talin | 2000-3000 |

In embodiments in which the customization agent comprises a sweetening agent, prior to customization the dosage form may comprise the same sweetening agent, a different sweetening agent, or in one particular embodiment, no sweetening agent at all. In certain embodiments, the dosage form is substantially free of the particular sweetening agent to be delivered. For example, the sweetening agent to be delivered may be selected from high intensity sweeteners, and the dosage form may be substantially free of high intensity sweeteners. As used herein, "high intensity sweeteners" are those having a sweetness index greater than 1.0. Suitable high intensity sweeteners for use in the customization agent include but are not limited to aspartame, sucralose, acesulfame, saccharin, and pharmaceutically acceptable salts and combinations thereof.

In one embodiment of the invention, the customization agent comprises a coloring agent. Here, the dosage form may be provided as a colorless liquid (i.e., clear or opaque) or have a first color. If the dosage form has a first color, which is provided by a first coloring agent, the customization agent has a second color provided by a second coloring agent that is preferably, but not necessarily, different from the first color. After combining the dosage form and the customization agent the finished product, i.e., the customized dosage form, may take on the color of the customization agent, or become a new color altogether. If the dosage form initially has a first color, the customized dosage form may exhibit dual colors, that is, distinct regions of each color, such as a swirl of two separate colors, or small or large areas (i.e., dots) of one color within the other color.

In another embodiment of the invention, the customization agent comprises a flavoring agent. In this embodiment, the dosage form is provided with a first flavoring agent having a first flavor and the customization agent comprises a second flavoring agent having a second flavor. This is advantageous in that the dosage form has at all times in the hands of the consumer at least some acceptable flavor. Dosage forms without any flavoring agent typically taste unpleasant. Accidental ingestion of an unflavored dosage form, although not harmful, may prejudice a patient, particularly a pediatric patient, against further administration. Having at least some acceptable flavor in the dosage form is therefore desirable.

The first and second flavors are preferably, but not necessarily, different. Accordingly, the customized dosage form may take on the second flavor, or may be imparted with a new, third flavor. Alternatively, the dosage form may be imparted with dual flavors, that is, both the first and second flavors are perceptible to the patient simultaneously.

In one embodiment, the customized dosage form delivers sequential flavors to the patient, that is, the first flavor is perceptible to the patient before the second flavor, or vice-versa. In one embodiment, for example, the patient perceives the first flavor substantially absent of the second flavor for some period of time, then optionally the patient perceives both flavors for a period of time, but at varying levels of intensity, then finally the patient perceives the second flavor substantially absent of the first flavor for a period of time. In another embodiment, the patient perceives both the first and second flavors initially, followed by a period of time during which the intensity of the first flavor decreases, and the patient continues to perceive the second flavor after the perception of the first flavor has diminished or ended.

For example, the flavoring agent may persist in the oral cavity until after all or substantially all of the liquid dosage form has been swallowed so that the patient continues to perceive the second flavor after the dosage form has been swallowed. The flavoring agent may be a solid of particular shape or other physical or chemical property that has a certain adhesion or surface tension in the oral cavity. In one particular embodiment, the flavoring agent is in the form of flaked films that become suspended in the dosage form upon combination therewith. The flaked films, which preferably have a thickness of about 0.05 mm, coat the surfaces of the oral cavity and are held in place there until after all of the dosage form has been swallowed.

Suitable flavoring agents are for example those proprietary blends of chemicals commercially available from various flavor companies, for example, International Flavors and Fragrances, Busch Boake Allen, and Firmenich. Typical flavors to be imparted by these flavoring agents include but are not limited to fruit flavors such as cherry, berry, citrus, apple, grape, watermelon, and the like; candy flavors such as chocolate, vanilla, caramel, bubblegum, cotton candy, and the like; and mint flavors such as peppermint, spearmint, cinnamon, menthol, and the like.

In another embodiment of the invention, the customization agent comprises a texturizing agent. Here, the dosage form may initially have a smooth, gritty, or other first texture. The texturizing agent has a second texture that may be different from or similar to the first texture. After combining the dosage form and the customization agent, the dosage form may take on the texture of the texturizing agent, or have a new texture altogether. The customized dosage form may exhibit dual textures, that is, distinct regions of each texture, such as a swirl of two separate textures, or small or large areas of one texture within the other texture.

In certain embodiments, the customization agent is packaged in a unit amount suitable for customizing one unit dose of the liquid dosage form. For example, the dose of a liquid dosage form may typically range from 1 to about 4 teaspoonfuls of liquid to be administered to a patient depending on the age and weight of the patient. In this case, the unit amount of customization agent will be suitable for customizing from about 1 to about 4 teaspoonfuls of the liquid dosage form. In one such embodiment, in which the customization agent is in the form of a multiparticulate solid, such as a dry powder, granules, crystals, or comminuted flaked films, the customization agent may be provided in a blister, pouch, or truncated straw, shaped to facilitate pouring of the multiparticulate solid customization agent into a unit dose of the liquid dosage form.

In certain other embodiments, the customization agent is packaged in an amount suitable for customizing one bottleful of the liquid dosage form. Form example, a bottle of a liquid dosage form may contain 1 ounce, 2 ounces, 3 ounces, 4 ounces, or 6 ounces of the liquid dosage form. In one such embodiment, in which the customization agent is in the form of a multiparticulate solid, such as a dry powder, granules, crystals, or comminuted flaked films, the customization agent may be provided in a blister, pouch, cup, or sealed straw, shaped to facilitate pouring of the multiparticulate solid customization agent into a bottle of the liquid dosage form. In such embodiments, the customization agent is designed and tested to be physically and chemically compatible with the liquid dosage form for the typical use life of the entire bottle.

The invention also provides a kit, which comprises one or more customization agents for combining with one or more dosage forms. In one embodiment, the kit comprises a first container containing one or more dosage forms and a second container containing one or more customization agents as described above. The first container may contain multiple doses of the same dosage form, or a plurality of different dosage forms. Likewise, the second container may contain a plurality of the same customization agent or a plurality of different customization agents. In another embodiment, the kit comprises at least a first container containing one or more doses of a dosage form, and a plurality of containers containing measured doses of customization agent. In one particular embodiment the kit comprises customization agent for use with dosage forms which are provided and/or purchased separately from the kit. The kit may include instructions for combining and/or using the dosage forms and customization agents.

The first container, or the containers for the dosage form, may, for example, be a bottle, pouch, unit dose cup, or bulk container containing a plurality of unit dose containers. The second container or the plurality of containers for the customization agent, may be a blister, pouch, cup, straw, bottle, dropper, or matchbook, or a bulk container containing a plurality of unit dose containers.

In certain preferred embodiments the kit comprises a plurality of containers, each containing a measured amount of the customization agent, the amount of customization agent in each container being a unit amount suitable for customizing one unit dose of the dosage form. In these embodiments, the number of containers of customization agent are preferably selected to correspond approximately to the number of doses of the dosage form in the kit. For example, a 4 ounce bottle of Acetaminophen suspension having 160 mg of acetaminophen per teaspoonful contains about 8 to 24 doses, depending upon the age and weight of the patient. Accordingly, the kit may typically contain about 8 to about 24, e.g. about 12 to about 20 individual containers of customization agent.

The kit may comprise any number of containers of dosage form, and any number of containers of customization agent. For example, a kit may contain two 2-ounce bottles of liquid dosage form, and from about 12 to about 24 unit amount containers of customization agent. In another example, a kit may contain 2 4-ounce bottles of liquid dosage form, and from about 24 to about 40 unit amount containers of customization agent. In another example, a kit may contain one 4-ounce bottle of liquid dosage form, and from about 8 to about 24 unit amount containers of customization agent.

In one embodiment, the dosage form comprises a liquid matrix containing an active ingredient, a first flavoring agent having a first flavor, and a plurality of particles comprising a second flavoring agent having a second flavor. The liquid matrix may be a liquid or semi-liquid, the dosage form accordingly being in the form of a syrup, suspension, solution, or emulsion. The active ingredient and first flavoring agent may be dissolved in the liquid matrix or suspended in the liquid matrix, depending on the nature of the liquid matrix, active ingredient and first flavoring agent. The particles comprising the second flavoring agent are suspended in the liquid matrix, and in a preferred embodiment comprise flaked films as described above.

In certain preferred embodiments, the dosage form is a liquid pharmaceutical oral suspension comprising at least one active ingredient and a suitable suspending vehicle. In a pharmaceutical suspension, typically at least one active ingredient is present substantially in the form of undissolved solid particles. In certain embodiments of the invention, the suspended particles contain active ingredient. These are referred to herein as "active particles" or "active ingredient particles." In one embodiment, the suspended particles are substantially pure crystals of the active ingredient having a median particle size (d50%) from about 5 to about 11 microns. In another embodiment, the suspended particles are agglomerates, e.g. granules, comprising active ingredient. In another embodiment, the suspended particles further comprise a coating on their surface, e.g. a polymer coating for the purpose of tastemasking or modified release. Suitable particle coating systems for tastemasking are known in the art.

The active ingredient or ingredients are present in a "unit dose volume" of the oral suspension in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regimen, the age and weight of the patient, and other factors must be considered, as known in the art. As used herein a "unit dose volume" of the oral suspension is a convenient volume for dosing the product to a patient. The dosing directions instruct the patient to take amounts that are multiples of the unit dose volume depending on, e.g., the age or weight of the patient. Typically the unit dose volume of the suspension will contain an amount of active ingredient that is therapeutically effective for the smallest patient. For example, suitable unit dose volumes may include one teaspoonful (about 5 mL), one tablespoonful (about 15 mL), one dropper, or one milliliter.

In one embodiment, the oral pharmaceutical suspension composition in accordance with the present invention is an aqueous suspension comprising from about 0.05% to about 40%, e.g. about 0.05 to about 0.2%, or about 1.6 to about 10%, or about 15 to about 40% weight per volume (w/v) of at least one active ingredient. It is possible that more than 40% of a water insoluble active ingredient could be included in the suspension. Suspensions containing less than 0.05% of active ingredients are also possible.

In one embodiment, in which the active ingredient is loratadine, the level of active ingredient in the suspension is preferably from about 2.5 to about 5 milligrams per teaspoonful, or from about 0.05 to about 0.2% w/v. In another embodiment, in which the active ingredient is acetaminophen, the level of active ingredient in the suspension is from about 80 to about 160 mg per teaspoonful, or about 1.6 to about 3.2% w/v. In another embodiment, in which the active ingredient is acetaminophen, the level of active ingredient in the suspension is preferably from about 80 to about 160 mg per 1.6 mL, or about 5 to about 10% w/v. In another embodiment, in which the active ingredient is ibuprofen, the level of active ingredient in the suspension is from about 50 to about 200 mg, e.g. about 100 mg per teaspoonful, or about 40 mg per 1 mL, or about 1 to about 4% w/v.

In another embodiment, in which the active ingredient is ibuprofen, the level of active ingredient in the suspension is preferably from about 20 to about 40 mg/mL, or about 2% to about 4% w/v, or about 100 to about 200 mg per teaspoonful.

The suspensions of the present invention can employ suspending systems as known in the art. The suspending system typically comprises one or more structuring agents that may be selected from hydrophilic polymers such as hydrocolloids, swelling or gelling polymers, and the like. In one preferred embodiment, the suspending system additionally comprises a swelling agent.

A structuring agent, when introduced into an appropriate aqueous environment, forms an ordered structure, stabilized by hydrogen bonding and molecular entanglement. Hydrocolloids are a particularly good type of structuring agent. Hydrocolloids are dispersions of particles around which water molecules and solvated ions form a shell-like structure, fluid absorption occurs principally by swelling and enlargement of the structure.

Examples of suitable hydrocolloids include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan, rhamsan, zooglan, methylan, chitin, cyclodextrin, chitosan, and combinations thereof. In certain embodiments of the present invention, xanthan gum is a preferred hydrocolloid for use as a structuring agent.

Xanthan gum is a high molecular weight natural carbohydrate, specifically, a polysaccharide. The xanthan gum suitable for use in the present invention is a high molecular weight polysaccharide produced by Xanthomonas campestris. Techniques and strains for producing this polysaccharide are described in U.S. Pat. Nos. 4,752,580 and 3,485,719 (the disclosures of which are hereby incorporated by reference). The xanthan gum used in the present invention should have a viscosity in a one percent salt solution of from about 1000 to about 1700 cP (mPa-sec). The one percent solution's viscosity should be measured at 25° C. with an LV model Brookfield Synchro-Lectric viscometer at 60 rpm, no. 3 spindle. Xanthan gum is available from several commercial suppliers such a RT Vanderbilt Company and CP Kelco. Examples of suitable xanthan gums are Keltrol, Keltrol F, Keltrol T, Keltrol TF and Keltrol 1000 Keltrol, Keltrol TF and Keltrol 1000 are the xanthan gums for use in pharmaceutical suspensions.

A swelling agent, when exposed to an appropriate aqueous environment, expands without forming a network system. Pregelatinized starch is a particularly good swelling agent. Pregelatinized starch, also known as "instantized" starch, is precooked so that it swells and begins to thicken instantly when added to cold water. One particularly suitable pregelatinized starch is prepared from modified, stabilized and waxy, maize food starch, and commercially available from National Starch Company as INSTANT STARCH, ULTRASPERSE-M. Microcrystalline cellulose is another useful swelling agent.

In certain preferred embodiments of the present invention, the combined use of a structuring agent and a swelling agent as a blended thickening component is an important feature for achieving the desired liquid suspension. The use of xanthan gum with a pregelatinized starch has been found to be a particularly advantageous combination.

Additionally, the suspensions of the present invention may comprise various adjuvants and excipients such as emulsifying agents, taste modifying compositions, preservatives, and the like. Suitable emulsifying agents and suspending agents include any food grade materials, such as mono and diglycerides, TWEENS and SPANS, lecithin, polyglycerol esters, propylene glycol esters and the like, Polysorbates, mono and diglycerides of fatty acids, sucrose fatty acid esters and polyoxyethylene derivatives of sorbitan fatty acid esters. Taste modifying compositions in accordance with the invention include but are not limited to sugars, sweet polyhydric alcohols, glycerin, artificial sweetener, flavoring agents and mixtures thereof. Examples of sugars include sucrose, fructose, dextrose, and glucose. Examples of sweet polyhydric alcohols include sorbitol and mannitol. Examples of high intensity sweeteners include aspartame, sucralose, cyclamates, asulfame K, saccharin and mixtures thereof. Preservatives useful in the present invention include, but are not limited to, benzoic acid and its pharmaceutically acceptable salts, e.g. sodium benzoate; sorbic acid and its pharmaceutically acceptable salts, e.g. potassium sorbate; and parabens (such as methyl, ethyl, propyl and butyl p-hydroxybenzoic acids esters). Preservatives, for purposes of this application, mean an antimicrobial agents.

EXAMPLE 1

A kit is provided to consumers. The kit contains one 4-ounce bottle of over-the-counter acetaminophen suspension, and 20 individual pouches representing 4 flavors of a customization agent, along with instructions for their use. The individual pouches are provided in a water-resistant re-seal able pouch for easy transporting and storage. The re-seal able pouch includes a separate set of instructions to ensure proper usage at all times. The instructions optimize the consumer dosing and flavor experience by directing consumers to fill the dosage cup with suspension first and then add the customizing agent.

The acetaminophen suspension is prepared according to the method described in U.S. Pat. No. 5,409,907, which is incorporated herein by reference. The appropriate dose of this particular product is 1 to 3 teaspoonfuls every 4-6 hours, depending upon the age and weight of the patient. The 4 ounce bottle therefore contains 8 to 24 doses, depending on the age and weight of the patient. The acetaminophen suspension comprises one or more flavoring agents that impart the product with a cherry flavor.

The customization agent is a flaked film commercially available from Watson Foods Co., Inc. as "insoluble edible glitter." The customization agent is provided as 0.2 grams of material in each packet. The packets are formed in the shape of a thin stick. Of the 20 individual packets of customization agent provided with each kit, a first portion comprise flavoring agent which imparts one type of flavor, and additional portions comprise flavoring agents which impart different flavors, optionally including sensation agents and coloring agents. In this example, one option the consumer may select is a customization agent which comprises one or more flavoring agents to impart a cola flavor, along with a sensation agent to impart a tingling sensation, and one or more coloring agents which impart a red color to the flaked film.

The instructions direct a parent or care-giver to dispense a measured dose of the acetaminophen suspension in a dosing cup, then add one packet of customization agent to the suspension in the dosing cup, without stirring, then administer the customized dosage form to a pediatric patient within about 5 minutes of combining the ingredients.

EXAMPLE 2

A consumer test was conducted to assess children's reaction to Children's Tylenol® Oral Suspension Pain Reliever customized with flavored flaked films. One hundred and six children (male and female, ages 6-10, Tylenol® users) were provided a weight appropriate dose of either cherry or grape flavored Children's Tylenol® and asked to select a flavored flaked film from an array (bubble gum, strawberry, chocolate, sour apple, cola). 0.3 gram of flaked film (1/16 teaspoon) was applied to the top of the dose by the experimenter to customize the Children's Tylenol®. Children were asked to consume the entire amount as normal, and then were asked a series of taste-related questions. A control cell comprised of 30 children was also run. These children were given a weight appropriate dose of Children's Tylenol® without the film flakes and asked to consume the product as normal. They were then asked a similar series of taste questions.

The following results were obtained:

1. The customized dosage forms containing flaked films significantly reduced the aftertaste of Children's Tylenol®. After consuming the dose of customized Children's Tylenol®, the children were asked the question, "[N]ow that the medicine is gone, do you have any bad aftertaste left in your mouth?" A significantly greater percentage of children who consumed the customized Children's Tylenol® (85.5%) reported no bad aftertaste compared to those children that received the regular Children's Tylenol® (63.6%):

|  | PANEL | |
| --- | --- | --- |
|  | Control | Flaked Film |
| Yes, a lot | 4.5% | 2.6% |
| Yes, a little | 31.8 | 11.8 |
| No | 63.6 | 85.5 |
| Chi Square | 5.39 | |
|  | .068 | |

2. The customized Children's Tylenol® provided a significantly longer lasting flavor experience. All children who consumed the customized Children's Tylenol® with flavored flaked films were asked the question, "[D]id the flavor last longer than the medicine you take without the glitters?" A significantly larger percentage of children (69.2%) indicated that the customized Children's Tylenol® had a longer lasting flavor than medicine they take without the flaked films:

| % Stating flavor lasted longer | 69.2% |
| --- | --- |
| % Stating flavor did not last longer | 20.8% (n = 94; p < .05) |

3. The children were able to distinguish two sequentially-distinct flavors in the customized Children's Tylenol®. All children who consumed the customized Children's Tylenol® were asked the question, "[W]ere you able to taste two different flavors?" A significantly larger percentage of children (80.2%) responded that they were able to taste both flavors either a little or a lot compared to children reporting they could not taste two flavors:

| | |
|---|---|
| % stating able to taste 2 flavors: | 80.2% |
| % stating not able to taste 2 flavors: | 19.8% (n = 106; p < 0.05) |

Upon further examination, a larger proportion of children indicated they tasted the flavor of the liquid medicine (Children's Tylenol®) first (51.4%) vs. the flavor of the flaked films (44.8%). After waiting approximately one minute, a reverse trend was found. Of those still perceiving a flavor, a great percentage of children indicated they tasted the flavor of the flaked films (39%) vs. those indicating they tasted the flavor of the medicine (30%).

4. The flaked films enhanced the overall palatability of Children's Tylenol® suspension, leading to a more likeable taste. All children who consumed the customized Children's Tylenol® were asked the question, "[H]ow much do you like the way this tastes?" A significantly larger percentage (84%) rated the sample positively (taste great/good) vs. those who rated the sample neutral or negatively (okay, not good, terrible) (16%):

| | |
|---|---|
| % rating taste good/great | 84% |
| % rating taste okay/not good/terrible | 16% (n = 106; p < 0.01) |

EXAMPLE 3

A kit is provided to consumers. The kit contains one 4-ounce bottle of over-the-counter ibuprofen suspension, and 15 individual pouches representing 5 flavors of a customization agent, along with instructions for their use. The ibuprofen suspension is prepared according to the method described in U.S. Pat. No. 5,374,659, which is incorporated herein by reference. The ibuprofen suspension comprises one or more flavoring agents that impart the product with a grape flavor. The customization agent is a flaked film commercially available from Watson Foods Co., Inc. as "slow soluble edible glitter WT-7474A." The customization agent comprises one or more flavoring agents to impart an apple flavor, along with a sensation agent to impart a cooling sensation, and one or more coloring agents that impart a green color to the flaked film. The 15 individual pouches of customization agent are packaged together in a water-resistant re-seal able pouch for easy transporting and storage. The re-seal able pouch includes a separate set of instructions to ensure proper usage at all times. The instructions optimize the consumer dosing and flavor experience by directing consumers to fill the dosage cup with suspension first and then add the customizing agent.

We claim:

1. A liquid pharmaceutical dosage form comprising a liquid matrix containing an active ingredient, a first flavoring agent having a first flavor, and a plurality of particles comprising a second flavoring agent having a second flavor wherein said particles comprise flaked films that are suspended in the liquid matrix.

2. The dosage form according to claim 1, wherein said dosage form is selected from the group consisting of syrups, suspensions, solutions, and emulsions.

3. The dosage form according to claim 1, wherein the flaked films have a thickness of about 0.01 to about 0.25 mm.

4. The dosage form according to claim 1, wherein the flaked films comprise a film-former selected from the group consisting of gum arabic, pullulan, starch, maltodextrins, pectin, hydroxypropylmethylcellulose, alginates, carrageenans, and derivatives and combinations thereof.

5. The dosage form according to claim 1, wherein the flaked films comprise multiple layers.

6. The dosage form according to claim 1, wherein the flaked films comprise holes.

7. The dosage form according to claim 1, which, upon ingestion, delivers the first and second flavors sequentially in any order.

8. The dosage form according to claim 7, which, upon ingestions, delivers the first flavor, followed by a combination of the first and second flavors.

9. The dosage form according to claim 7, which, upon ingestion, delivers a combination of the first and second flavors, followed by substantially only the second flavor.

10. The dosage form of claim 8, which further delivers substantially only the second flavor following delivery of the combination of the first and second flavors.

11. The dosage form of claim 7, which, upon ingestion, delivers the second flavor, followed by a combination of the first and second flavors.

12. The dosage form of claim 7, which upon ingestion, delivers a combination of the first and second flavors, followed by substantially only the first flavor.

13. The dosage form of claim 1, wherein said dosage form is an over-the-counter product.

14. The dosage form according to claim 3, wherein the flaked films comprise a film-former selected from the group consisting of gum arabic, pullulan, starch, maltodextrins, pectin, hydroxypropylmethylcellulose, alginates, carrageenans, and derivatives and combinations thereof.

15. The dosage form according to claim 3, wherein the flaked films comprise multiple layers.

16. The dosage form according to claim 4, wherein the flaked films comprise multiple layers.

17. The dosage form according to claim 14, wherein the flaked films comprise multiple layers.

18. The dosage form according to claim 3, which, upon ingestion, delivers a combination of the first and second flavors, followed by substantially only the second flavor.

19. The dosage form according to claim 4, which, upon ingestion, delivers a combination of the first and second flavors, followed by substantially only the second flavor.

20. The dosage form according to claim 5, which, upon ingestion, delivers a combination of the first and second flavors, followed by substantially only the second flavor.

* * * * *